United States Patent [19]

Kenyon

[11] Patent Number: 4,684,368
[45] Date of Patent: Aug. 4, 1987

[54] INVERTED PUMP
[75] Inventor: Richard L. Kenyon, Irvine, Calif.
[73] Assignee: Parker Hannifin Corporation, Cleveland, Ohio
[21] Appl. No.: 882,218
[22] Filed: Jul. 3, 1986

Related U.S. Application Data

[63] Continuation of Ser. No. 616,370, Jun. 1, 1984, abandoned.

[51] Int. Cl.⁴ .................................................. A61M 5/00
[52] U.S. Cl. ............................ 604/152; 128/DIG. 12; 417/417; 604/891
[58] Field of Search ............... 604/67, 246, 890, 891, 604/892, 151, 152; 128/DIG. 12, DIG. 13; 417/417, 240

[56] References Cited

U.S. PATENT DOCUMENTS

| 4,300,552 | 11/1981 | Cannon | 604/246 |
| 4,316,460 | 2/1982 | Genese et al. | 604/246 |
| 4,364,386 | 12/1982 | Jenkins et al. | 604/151 |
| 4,482,346 | 11/1984 | Reinicke | 128/DIG. 12 |
| 4,486,190 | 12/1984 | Reinicke | 604/891 |
| 4,493,709 | 1/1985 | Smith | 604/246 |
| 4,525,165 | 6/1985 | Fischell | 604/891 |

FOREIGN PATENT DOCUMENTS 2025368 1/1980 United Kingdom ....... 128/DIG. 13

Primary Examiner—Stephen C. Pellegrino
Attorney, Agent, or Firm—Christopher H. Morgan

[57] ABSTRACT

A pump wherein an armature (64) is reciprocated between an electromagnetic core (54) and a housing (48). A diaphragm (68) is responsive to movement of the armature (64) and cooperates with a body (10) to form a pumping chamber (80). Expansion of the pumping chamber (80) by spring (66) draws fluid through a valve (20) at a slow rate. Contraction of the pumping chamber (80) by electromagnetic attraction of armature (64) to core (54) expels fluid through valve (42).

4 Claims, 1 Drawing Figure

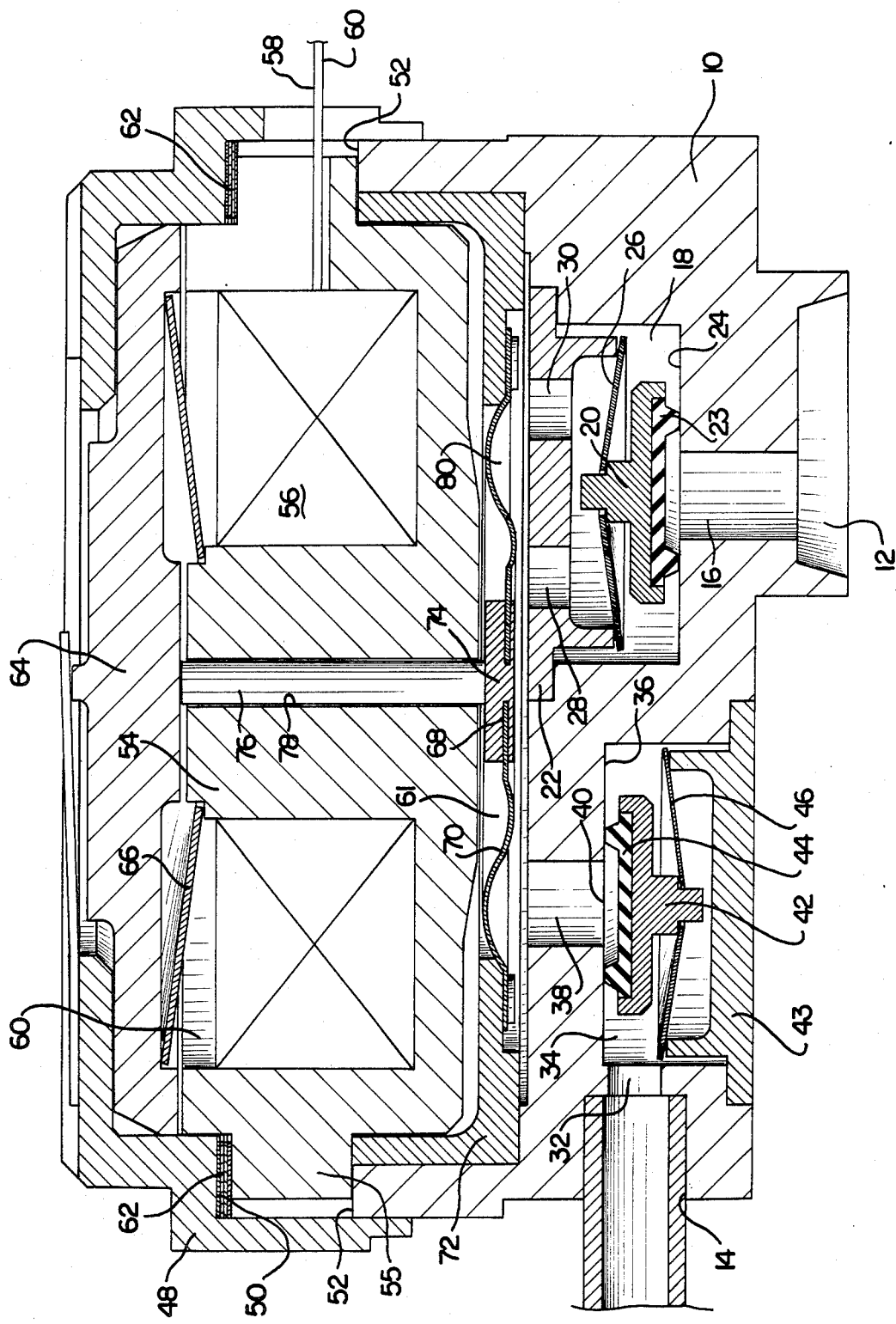

INVERTED PUMP

This application is a continuation of application Ser. No. 616,370, filed June 1, 1984, now abandoned.

BACKGROUND OF THE INVENTION

1. Field of the Invention

The subject invention is directed to pumps for medication systems and, more particularly, reciprocating pumps suitable for use in human implantable medication systems.

2. Description of the Prior Art

Many examples of implantable medical devices intended for unfusing medication intimed dosages are known in the prior art. Early devices were basically pressurized reservoirs from which the medication was to be controllably gated into a catheter. One disadvantage of such devices was that in certain failure modes, they could potentially discharge uncontrolled amounts of medication into the user. To overcome this, such devices typically included somewhat elaborate safety mechanisms. Examples are shown in U.S. Pat. Nos. 4,193,397; 4,221,219; 3,731,681; 4,299,220; 3,894,538; and 3,951,147.

Subsequently, it was recognized that a device wherein the medication in a reservoir could be maintained below atmospheric pressure would be inherently safer since the potential for discharging uncontrolled amounts of medication did not exist. However, the operation of these devices required the medication to be actively pumped from the reservoir. Example are shown in U.S. Pat. No. 4,373,527 and U.S. patent application Ser. No. 439,138, filed Nov. 11, 1982 by Robert E. Fischell. Generally, the medication devices used a battery to charge a capacitor that was discharged to drive the pump solenoid. The pumps were arranged such that closure of the pump solenoid powered the suction stroke for the pump. This stroke would establish a suction in the pump cavity that would draw medication from the reservoir into the pump chamber. When the capacitor current dissipated and the solenoid was de-energized, a spring in the pump would mechanically open the pump solenoid. This stroke would elevate the pressure in the pump chamber and cause the medication therein to be expelled through the output port.

While such prior devices afforded many advantages, a disadvantage was that entrained air in the medication could collect to form a bubble inside the chamber of the pump. Because the solenoid closed relatively quickly in response to the current pulse from the capacitor, the intake stroke was rapid and required the liquid to flow at a high rate through the input valve. This resulted in a large pressure drop between the reservoir and pump chamber and relatively low absolute pressure in the pump chamber. In this way, pumps of prior art devices tended to draw entrained air out of the medication and create bubbles. Due to the relatively high elasticity of air, air bubbles in these devices could potentially compromise their efficiency as well as the accuracy of the medication dosages that they administered.

In the prior art, various proposals have been advanced to avoid or remedy the formation of air bubbles in actively pumped medication systems. For example, in U.S. Pat. No. 4,360,019 a tube between the reservoir and the pump chamber is bent back on itself in a manner intended to block entry of bubbles from the reservoir into the tube. Alternatively, use of a filter in the fluid path between the pump and the reservoir has also been suggested. Similarly, U.S. Pat. No. 4,191,181 described the use of a wicklike member composed of lightly packed glass-like fibers that have sufficient capillary force to prevent gas from entering the fine channels.

However, such highly filtered systems tended to be prone to plugging by contaminant particles and could not be easily cleaned or changed once implanted in a patient. Moreover, they did not address the fact that dissolved or entrained air tended to form a bubble when exposed to low absolute pressures inside the medication pump.

An "inverted pump" operates conversely from the conventional pumps described above. In an "inverted pump" the solenoid is closed to drive the discharge stroke and the spring force drives the intake or suction stroke. During the suction stroke, an inverted pump could maximize absolute pressure in the pump chamber because the spring force could be selected to provide a slow intake of medication. However, none of the inverted pumps of prior art designs would operate in an efficient and repeatable manner suitable for the application of the subject invention.

For example, U.S. Pat. No. 4,152,098 discloses an inverted pump wherein an elastic diaphragm is stretched to permit the movement of a ball during the discharge stroke. The diaphragm then contracts to return the ball to its original position for the suction stroke. A pump of this design would require a diaphragm having sufficient elasticity to accommodate the movement of the ball over its entire stroke. At the same time the pump would require the diaphragm to develop sufficient force to overcome the pressure drop across the inlet check valve, the difference between the pump chamber pressure and the inlet pressure, the weight of moving parts, and friction forces. In a pump constructed in accordance with the design of the U.S. Pat. No. 4,152,098, a diaphragm having sufficient elasticity to accommodate the stroke of the ball, would not develop sufficient force to return the ball in a manner suitable for many applications where repeatability and efficiency are also important.

Accordingly, there was a need in the prior art for an inverted pump suitable for use in medication systems that would operate in an efficient and repeatable manner. Such a pump would maximize absolute pressure in the pump cavity during the intake stroke, thus decreasing the potential for establishing air bubbles in the pump.

SUMMARY OF THE INVENTION

In accordance with the subject invention, a pump includes a body that has a housing secured thereto. An electromagnet is secured between the body and the housing and an armature is located on one side of the electromagnet such that it is movable between the electromagnet and the housing. A spring that is located between the armature and the electromagnet loads the armature toward the housing. A partition that is located on the side of the electromagnet opposite from the spring is secured between the electromagnet and the body. The partition is responsive to movement of the armature and cooperates with the body to define a pump chamber.

Preferably, the electromagnet cooperates with the body to define a cavity for the partition and the partition has a first position adjacent the electromagnet when the armature contacts the housing and a second position adjacent the body when the armature contacts the electromagnet.

Also preferably, the partition is a diaphragm formed by a peripheral ring and a central disk connected to an annular membrane. The central disk is contacted by a stem that engages the armature and the peripheral ring is secured between the body and the electromagnet.

More preferably, the pump includes inlet and output valves that are biased toward their closed positions by Belleville springs.

Other details, objects and advantages of the subject invention will become apparent as the following description of a presently preferred embodiment thereof proceeds.

BRIEF DESCRIPTION OF THE DRAWING

The accompanying drawing shows an elevational cross-section of an inverted pump in accordance with the subject invention.

DESCRIPTION OF THE PREFERRED EMBODIMENT

As shown in the FIGURE, the preferred embodiment includes a body 10 having an inlet port 12 and an output port 14. Inlet port 12 communicates with a passageway 16 that leads to a valve chamber 18. A check valve 20 is located at the end of passageway 16 by a retainer 22. Check valve 20 includes a seal 23 and is biased in a closed position against a wall 24 of valve chamber 18 by a Belleville spring 26. Retainer 22 is provided with bores 28 and 30 such that when valve 20 is in the open position with seal 23 unseated from wall 24, bores 28 and 30 are in communication with passageway 16.

Output port 14 communicates with a passageway 32 that leads to a valve chamber 34. Valve chamber 34 includes a wall 36 that opens to a second passageway 38 through a port 40. A check valve 42 is located at port 40 by a retainer 43. Check valve 42 includes a seal 44 and is biased in a closed position with seal 44 engaging wall 36 adjacent the periphery of port 40 by a Belleville spring 46. When valve 42 is in the open position with seal 44 unseated from wall 36, passageway 38 is in communication with passageway 32 through chamber 34.

A housing 48 that includes a shoulder 50 is connected to one end of body 10 adjacent an end face 52. Shoulder 50 of housing 48 cooperates with end face 52 of body 10 to secure an electromagnetic means therebetween. The electromagnetic means of the preferred embodiment includes an electromagnetic core 54 having an annular ring 55 and an electric coil 56 with leads 58 and 60. Coil 56 is fastened in a channel 60 of core 54. In the specific example of the preferred embodiment, annular ring 55 of core 54 is secured between shoulder 50 and end face 52. Thus secured between housing 48 and body 10, core 54 cooperates with body 10 to define an internal cavity 61. Shims 62 are also provided between shoulder 50 of housing 48 and annular ring 55 of core 54 to better align and locate housing 48 with respect to core 54.

An armature 64 is located on one side of core 54 between core 54 and housing 48. Armature 64 is movable between housing 48 and core 54. When core 54 and coil 56 are not energized, a Belleville spring 66 that is located between armature 64 and core 54 loads armature 64 against housing 48 and away from core 54. Energization of core 54 and coil 56 sufficient to overcome the loading force of spring 66 draws armature 64 into contact with core 54.

A partition such as diaphragm 68 is located adjacent the side of core 54 that is oppositely disposed from armature 64 and spring 66. Diaphragm 68 includes an annular membrane 70 that is connected to a peripheral ring 72 and a central disk 74. A stem 76 extends through a central bore 78 of core 54 and is longitudinally movable therein. Stem 76 contacts disk 74 and engages armature 64 such that disk 74 is responsive to movement of armature 64 through stem 76. Diaphragm 68 cooperates with body 10 to define a pump chamber 80 therebetween.

In the operation of the preferred embodiment, armature 64 is reciprocated between housing 48 and core 54 by periodically overcoming the mechanical loading force of spring 66 with the electromagnetic force of core 54 and coil 56. The movement of armature 64 is translated through stem 76 to control disk 74 and annular membrane 70 in response to movement of the armature. Specifically, disk 74 moves between a first position adjacent core 54 when armature 64 contacts housing 48 and a second position adjacent body 10 when aramature 64 contacts core 54. The movement of disk 74 and annular membrane 70 between these first and second positions causes the volume of pump chamber 80 to expand and contract. This change in volume causes fluid to be pumped from inlet port 12 through valve 20, chamber 80, and valve 42 to output port 14.

More specifically, under static conditions with no electromagnetic force from core 54 and coil 56, the loading force of spring 66 is adequate to gently urge armature 64 against housing 48. Thus, diaphragm 68 is in the first position adjacent core 54 and chamber 80 is at maximum volume. When diaphragm 68 is in the first position under static flow conditions, chamber 80 is filled with fluid and valves 20 and 42 are in their respective closed positions. When sufficient electrical current is thereafter supplied on leads 58 and 60, core 54 and coil 56 cooperate to apply an electromagnetic force to armature 64 that is sufficient to overcome the loading force of spring 66 and draw armature 64 into contact with core 54.

The closing movement of armature 64 is translated to disk 74 through stem 76 so that diaphragm 68 is moved to the second position adjacent body 10 and chamber 80 is decreased to its minimum volume. As the volume of chamber 80 decreases, the pressure therein increases and acts through bores 28 and 30 to urge valve 20 more tightly closed and through passageway 38 to urge valve 42 open. When pressure in chamber 80 exceeds the set pressure of valve 42, valve 42 opens and fluid flows past seal 44 and through valve chamber 34 and passageway 32 to output port 14. When sufficient fluid has been expelled that pressure chamber 80 falls below the set pressure of valve 42, the valve closes and flow is stopped.

When current to leads 58 and 60 is discontinued, core 54 is de-energized and spring 66 returns armature 64 to its position in contact with housing 48. This movement of armature 64 returns diaphragm 68 to its first position and expands the volume of chamber 80 from its minimum value to its maximum value. As chamber 80 expands, with valves 20 and 42 closed, absolute pressure in chamber 80 decreases. When this pressure falls below the pressure drop across valve 20, valve 20 opens and fluid flows through passageway 16, past seal 23, and through chamber 18 and bores 28 and 30 into chamber 80. As is hereafter more fully explained, the loading force of spring 66 is established to limit the pressure differential between inlet 12 and the pressure in chamber 80. When armature 64 is in contact with housing 48 and the pressure drop from inlet 12 to chamber 80 falls below the set pressure of valve 20, the valve closes and the pump cycle is complete.

In accordance with the subject invention, the loading force of spring 66 is established so that, on the intake stroke of diaphragm 68, the pump herein disclosed maintains higher absolute pressure in chamber 80 than pumps used in the prior art. This higher absolute pressure tends to avoid drawing entrained or dissolved air out of the fluid to form air bubbles in chamber 80. More specifically, the design of spring 66 is selected such that the loading force is sufficient to overcome opposing frictional and gravitational forces together with the set pressure or pressure drop across inlet valve 20 and to provide for a small pressure difference between chamber 80 and inlet 12. The small pressure difference between chamber 80 and inlet 12 results in a relatively slow rate of fluid flow into chamber 80. However, the suction stroke of the pump is mechanically powered by spring 66 and not electromagnetically by core 54 and coil 56. Thus, the time constraints for electromagnetic operation of prior art pumps during the suction stroke simply have no application to the pump of the subject invention.

Preferably, the set pressure of valve 20 as established by spring 26 is also maintained as low as system consideations will permit. This will further contribute to higher absolute pressure in chamber 80 that is sufficient to establish flow through valve 20.

Preferably, spring 26 is a Belleville spring or equivalent spring that produces a substantially constant force over the operating stroke of valve 20. In this way, the pressure drop across valve 20 remains substantially constant over the operating range of flow rates through valve 20.

A further benefit of limiting the loading force of spring 66 is an improvement in the efficiency of the pump. That is, the use of a spring 66 having lighter loading force permits the use of a smaller core 54 and coil 56 that are required to overcome the spring force during the output stroke. The smaller core 54 and coil 56 can thus perform the same function as a larger core and coil, but will have a lower power requirement.

While a presently preferred embodiment of the subject invention has been shown and described, the invention is not limited thereto but can be otherwise variously embodied within the scope of the following claims:

I claim:

1. A pump comprising:
   a body having an inlet port and an output port;
   a housing secured to one end of said body;
   an electromagnetic means having an internal passage, said electromagnetic means being secured between said body and said housing, said electromagnetic means cooperating with said body to define an internal cavity on one side of said electromagnetic means;
   an armature that is located on one side of said electromagnetic means that is opposite from said internal cavity, said armature being movable between said body and said housing, said armature contacting the one side of said electromagnetic means in response to energization of said electromagnetic means;
   a spring located between said armature and a portion of the side of said electromagnetic means that is opposite from said internal cavity and that is away from the internal passage of said electromagnetic means, said spring loading said armature toward said housing when said electromagnetic means is de-energized;
   a partition that is located in the internal cavity between said body and said electromagnetic means, and that cooperates with said body to define a pump chamber, said partition including an annular membrane, a peripheral ring attached to the periphery of said annular membrane, and a central disk that is connected to said annular membrane adjacent the center thereof; and
   a stem that extends through the internal passage of said electromagnetic means and that extends past said spring, said stem being secured to the central disk of said partition and to said armature such that said partition is movable in response to movement of said armature, said partition having a first position adjacent said electromagnetic means when said armature contacts said housing and a second position adjacent said body when said armature contacts said electromagnetic means.

2. The pump of claim 1 wherein said spring comprises a Belleville spring.

3. The pump of claim 1 wherein said housing includes a shoulder and said electromagnetic means includes a core having an annular band, said pump further comprising:
   a shim that is secured between the shoulder of said housing and the annular band of said core, said shim locating the position of said housing with respect to the core of the electromagnetic means to determine the stroke of said armature.

4. The pump of claim 1, 2, or 3 and further comprising:
   first and second valve means that are located adjacent said inlet port and said output port respectively, said first and second valves being biased in a closed position by springs.

* * * * *